United States Patent
Ohno et al.

(10) Patent No.: US 8,829,221 B2
(45) Date of Patent: Sep. 9, 2014

(54) METHOD FOR PRODUCING MONOSILANE AND TETRAALKOXYSILANE

(75) Inventors: Hiromoto Ohno, Tokyo (JP); Toshio Ohi, Tokyo (JP); Haruaki Ito, Tokyo (JP); Fanil Makhmutov, Moscow (RU)

(73) Assignee: Showa Denko K.K., Tokyo (JP)

( * ) Notice: Subject to any disclaimer, the term of this patent is extended or adjusted under 35 U.S.C. 154(b) by 676 days.

(21) Appl. No.: 13/125,606

(22) PCT Filed: Oct. 30, 2009

(86) PCT No.: PCT/JP2009/068648
§ 371 (c)(1),
(2), (4) Date: Apr. 22, 2011

(87) PCT Pub. No.: WO2010/050579
PCT Pub. Date: May 6, 2010

(65) Prior Publication Data
US 2011/0200513 A1  Aug. 18, 2011

(30) Foreign Application Priority Data
Oct. 31, 2008  (JP) .................................. 2008-281206

(51) Int. Cl.
*C07C 7/00* (2006.01)

(52) U.S. Cl.
USPC ...................................................... 556/454

(58) Field of Classification Search
USPC ...................................................... 556/454
See application file for complete search history.

(56) References Cited

U.S. PATENT DOCUMENTS

| | | | |
|---|---|---|---|
| 4,016,188 A | 4/1977 | Kötzsch et al. | |
| 4,904,460 A | 2/1990 | Wada et al. | |
| 5,110,991 A * | 5/1992 | Champion et al. | 568/618 |
| 6,686,495 B2 * | 2/2004 | Beller et al. | 558/411 |

FOREIGN PATENT DOCUMENTS

| | | | |
|---|---|---|---|
| EP | 337322 A2 * | 10/1989 | |
| JP | 61-270207 A | 11/1986 | |
| JP | 1-264922 A | 10/1989 | |
| JP | 2-169592 A | 6/1990 | |
| JP | 2001-19418 A | 1/2001 | |
| JP | 2002-69078 A | 3/2002 | |
| JP | 2002069078 A * | 3/2002 | |

OTHER PUBLICATIONS

Sung Soo Kim, Jun Tae Lee, and Sang Hyuck Lee, Bull. Korean Chem. Soc. 2005,. 26(6), 993-994.*

A. I. Shipilov,_A. B. Bykova, L. I. Elokhova, and S. M. Igumnov, Russ.Chem.Bull., Int.Ed., 2003, 52(2), 487-491.*

Eiichi Suzuki, et al., "Disproportionation of Triethoxysilane over KF/Al$_2$O$_3$ and Heat-Treated Hydrotalcite", Applied Catalysis A: General, 1998, pp. 7-10, vol. 167, No. 1.

* cited by examiner

*Primary Examiner* — Fereydoun G Sajjadi
*Assistant Examiner* — Kofi Adzamli
(74) *Attorney, Agent, or Firm* — Sughrue Mion, PLLC

(57) ABSTRACT

The present invention relates to method for producing monosilane and tetraalkoxysilane comprising subjecting alkoxysilane represented by formula (1)

$$H_nSi(OR)_{4-n} \qquad (1)$$

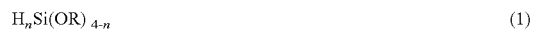

wherein R represents alkyl group having 1 to 6 carbon atoms and n represents an integer of from 1 to 3, to dismutation reaction in a gaseous phase in the presence of a catalyst containing an alkali metal fluoride and a catalyst activator.

The method can solve problems in a method for producing monosilane and tetraalkoxysilane by dismutation reaction of alkoxysilane in a liquid phase: i.e. problems such that separation from the solvent is difficult and that the reaction is too slow and not suitable for industrial production.

9 Claims, No Drawings

METHOD FOR PRODUCING MONOSILANE AND TETRAALKOXYSILANE

CROSS REFERENCE TO RELATED APPLICATION

This application is a National Stage of International Application No. PCT/JP2009/068648 filed Oct. 30, 2009, claiming priority based on Japanese Patent Application No. 2008-281206, filed Oct. 31, 2008, the contents of all of which are incorporated herein by reference in their entirety.

TECHNICAL FIELD

The present invention relates to a method for producing monosilane and tetraalkoxysilane by dismutation reaction of alkoxysilane.

BACKGROUND ART

Monosilane is useful as a volatile silicone material having high purity, and has been widely used for producing solar cells, semiconductors, amorphous photosensitive silicone materials and various ceramic materials.

Various methods for producing monosilane have been known to date. A method using reaction between magnesium silicide and acid or ammonium bromide, a method by reducing silicon chloride using $LiAlH_4$, a method by reducing silicon tetrafluoride using $CaH_2$ and a method by dismutation reaction of alkoxysilane have been known.

Trialkoxysilane is generally used as a starting material in the dismutation reaction of alkoxysilane, and monosilane and tetraalkoxysilane are produced according to the formula as follows:
[Chem. 1]

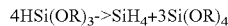
$$4HSi(OR)_3 \rightarrow SiH_4 + 3Si(OR)_4$$

Like monosilane, tetraalkoxysilane is a useful chemical material as a pure silicon precursor material for producing various silicon compounds for optical fibers, photomasks and IC sealing materials.

Triethoxysilane and trimethoxysilane are used as a starting material in the above-mentioned dismutation reaction and tetraethoxysilane and tetramethoxysilane are produced at the same time as monosilane, respectively, as shown in the following formulae.
[Chem. 2]

$$4HSi(OMe)_3 \rightarrow SiH_4 + 3Si(OMe)_4$$

$$4HSi(OEt)_3 \rightarrow SiH_4 + 3Si(OEt)_4$$

When the above reaction is conducted, metal sodium can be used as a catalyst of the dismutation reaction. However, the yield is low in the reaction and therefore the method was not practically useful.

Patent Document 1 discloses a method using alkali metal alkoxide or alkali metal silicate as a catalyst. However, the reaction in a liquid phase is too slow such that the reaction time exceeds ten hours, and therefore the method is not suitable for industrial production.

Patent Document 2 discloses a method for producing monosilane and tetraalkoxysilane by dismutation of alkoxysilane represented by formula $H_nSi(OR)_{4-n}$ wherein n is 1, 2 or 3 and R represents alkyl group or cycloalkyl group, comprising (i) a reaction step of obtaining monosilane and tetraalkoxysilane by dismutation of alkoxysilane in a solvent in the presence of a catalyst, (ii) a step of extracting part of the solvent containing a catalyst and tetraalkoxysilane after the reaction step, and (iii) a step of separating part or all of the tetraalkoxysilane by distilling the extracted solvent containing a catalyst and tetraalkoxysilane.

However, the method also employs dismutation reaction in a solvent and has had a problem of difficulties in separation from the solvent and a problem of insufficient reaction rate.
Patent Document 1: U.S. Pat. No. 4,016,188
Patent Document 2: JP-A-2001-19418

DISCLOSURE OF THE INVENTION

Problem to be Solved by the Invention

An objective of the present invention is to provide a method to solve problems as mentioned above that separation from the solvent is difficult and the reaction is too slow and not suitable for industrial production in a method for producing monosilane and tetraalkoxysilane by dismutation reaction of alkoxysilane.

Means to Solve the Problem

As a result of intensive studies to solve the above problems in the conventional art, the present inventors have found that the above problems can be solved by dismutation reaction of alkoxysilane represented by formula (1)
[Chem. 3]

$$H_nSi(OR)_{4-n} \tag{1}$$

wherein R represents alkyl group having 1 to 6 carbon atoms and n represents an integer of from 1 to 3, in a gaseous phase in the presence of a catalyst containing an alkali metal fluoride and a catalyst activator.

That is, the present invention relates to the following matters:

[1] A method for producing monosilane and tetraalkoxysilane comprising subjecting alkoxysilane represented by formula (1)
[Chem. 4]

$$H_nSi(OR)_{4-n} \tag{1}$$

wherein R represents alkyl group having 1 to 6 carbon atoms and n represents an integer of from 1 to 3, to dismutation reaction in a gaseous phase in the presence of a catalyst containing an alkali metal fluoride and a catalyst activator.
[2] The method as described in [1] above, wherein the alkali metal fluoride is potassium fluoride.
[3] The method as described in [2] above, wherein potassium fluoride is potassium fluoride dihydrate.
[4] The method as described in any one of [1] to [3] above, wherein the catalyst activator is tetrakis(dialkylamino)phosphonium halide represented by formula (2)
[Chem. 5]

$$(R^1R^2N)_4P^+X^- \tag{2}$$

wherein $R^1$ and $R^2$ represent alkyl group having 1 to 3 carbon atoms independently from each other and X represents Br, Cl or F.
[5] The method as described in [4] above, wherein tetrakis(dialkylamino)phosphonium halide is tetrakis(diethylamino)phosphonium bromide.
[6] The method as described in any one of [1] to [3] above, wherein the catalyst activator is 1,4-diazabicyclo[2.2.2]octane.
[7] The method as described in any one of [1] to [3] above, wherein the catalyst activator is hexaalkyl guanidinium halide represented by formula (3)

[Chem. 6]

$$[(R^3R^4N)_2CNR^5R^6]^+X^- \quad (3)$$

wherein $R^3$, $R^4$, $R^5$ and $R^6$ represent alkyl group having 1 to 3 carbon atoms independently from each other and X represents Br, Cl or F.

[8] The method as described in [7] above, wherein hexaalkyl guanidinium halide is hexaethyl guanidinium chloride.

[9] The method as described in any one of [1] to [3] above, wherein the catalyst activator is tetraalkyl ammonium chloride represented by formula (4)

[Chem. 7]

$$R^7R^8R^9R^{10}N^+Cl^- \quad (4)$$

wherein $R^7$, $R^8$, $R^9$ and $R^{10}$ represent alkyl group having 1 to 4 carbon atoms independently from each other.

[10] The method as described in [9] above, wherein tetraalkyl ammonium chloride is tetrabutyl ammonium chloride.

[11] The method as described in any one of [1] to [3] above, wherein the catalyst activator is calcium fluoride.

[12] The method as described in [2] above, wherein the alkali metal fluoride is potassium fluoride, the catalyst activator is calcium fluoride, potassium fluoride and calcium fluoride form potassium calcium trifluoride, and the integrated combination of the catalyst and the catalyst activator is used.

[13] The method as described in [11] above, wherein the alkali metal fluoride is potassium fluoride, the catalyst activator is calcium fluoride, potassium fluoride and calcium fluoride form potassium calcium trifluoride, and the integrated combination of the catalyst and the catalyst activator is used.

[14] The method as described in any one of [1] to [3] above, wherein the catalyst activator is oligo(ethylene glycol) dimethyl ether represented by formula (5)

[Chem. 8]

$$H_3C\text{—}O\text{—}(CH_2CH_2O)_m\text{—}CH_3 \quad (5)$$

wherein m is an integer of 2 to 8.

[15] The method as described in [1] above, wherein n in formula (1) is 1.

[16] The method as described in [15] above, wherein alkoxysilane represented by formula (1), in which n is 1, is trimethoxysilane.

Effects of the Invention

By subjecting alkoxysilane to reaction in a gaseous phase using a specific catalyst and a catalyst activator, the method of the present invention can solve the problems involved in a method for producing monosilane and tetraalkoxysilane by dismutation of alkoxysilane that separation from a solvent is difficult and the reaction rate is not sufficiently high.

BEST MODE FOR CARRYING OUT THE INVENTION

The method for producing monosilane and tetraalkoxysilane of the present invention is to be described in details below.

The present invention relates to a method for producing monosilane and tetraalkoxysilane, characterized in subjecting alkoxysilane represented by formula (1) to dismutation reaction in gaseous phase in the presence of a catalyst containing an alkali metal fluoride and a catalyst activator.

[Chem. 9]

$$H_nSi(OR)_{4-n} \quad (1)$$

(In the formula, R represents alkyl group having 1 to 6 carbon atoms and n represents an integer of from 1 to 3.)

Examples of alkoxysilane represented by formula (1) as a starting material of the dismutation reaction in the present invention include monoalkoxysilane, dialkoxysilane and trialkoxysilane. R represents alkyl group having 1 to 6 carbon atoms, and preferably alkyl group having 1 to 2 carbon atoms. Particularly preferred examples of alkoxysilane include monomethoxysilane, dimethoxysilane, trimethoxysilane, monoethoxysilane, diethoxysilane and triethoxysilane. Among these, trimethoxysilane and triethoxysilane are most preferable.

The dismutation reaction for the method of the present invention requires at least two components: i.e. a catalyst composition composed of a catalyst containing an alkali metal fluoride and a catalyst activator.

The first component of the catalyst composition is an alkali metal fluoride selected from a group of fluorides comprising MeF. Here, Me means alkali metal. Specifically, the alkali metal fluoride may contain LiF, NaF, KF or CsF. Among these, preferred are sodium fluoride, potassium fluoride and cesium fluoride.

The catalyst activator as the second component of the catalyst composition is selected from a group of the following organic or inorganic compounds.

First, tetrakis(dialkylamino)phosphonium halide represented by formula (2) can be used as a catalyst activator.

[Chem. 10]

$$(R^1R^2N)_4P^+X^- \quad (2)$$

(In the formula, $R^1$ and $R^2$ represent alkyl group having 1 to 3 carbon atoms independently from each other and X represents Br, Cl or F.)

Particularly, tetrakis(diethylamino)phosphonium bromide (($Et_2N)_4PBr$; which may be referred to as "TDAPB" hereinafter) can be preferably used as a catalyst activator. It is preferable to blend tetrakis(dialkylamino)phosphonium halide represented by formula (2) in an amount within the range of 0.1 to 20 parts by mass to 100 parts by mass of the alkali metal fluoride.

As a second catalyst activator, 1,4-diazabicyclo[2.2.2]octane (which may be referred to as "DABCO" hereinafter) may be used. In this case, not only DABCO but also cyclic tertiary amine having an aromatic and an aliphatic structure (for example, N, N'-dialkylpiperazine, N,N'-dialkyl-2,5-diazabicyclo[2.2.1]heptane and 1,5-diazabicyclo[4.3.0]non-5-en and pyrazine) related to DABCO is an effective organic catalyst activator. For example, commercially available potassium hydrogen fluoride (KF.HF) which is impregnated with a DABCO solution, dried and subjected to heat treatment may be used. It is preferable to blend DABCO in an amount within a range of 0.01 to 20 parts by mass to 100 parts by mass of alkali metal fluoride.

As a third catalyst activator, hexaalkyl guanidinium halide represented by formula (3) may be used.

[Chem. 11]

$$[(R^3R^4N)_2CNR^5R^6]^+X^- \quad (3)$$

(In the formula, $R^3$, $R^4$, $R^5$ and $R^6$ represent alkyl group having 1 to 3 carbon atoms independently from each other and X represents Br, Cl or F.)

Specifically, hexaethyl ganidinium chloride represented by $[(Et_2N)_2CNEt_2]Cl$ (which may be referred to as "HEGC" hereinafter) can be preferably used. It is preferable to blend hexaalkyl ganidinium halide represented by formula (3) in an amount within a range of 0.5 to 30 parts by mass to 100 parts by mass of alkali metal fluoride.

As a fourth catalyst activator, tetraalkyl ammonium chloride represented by formula (4) may be used.
[Chem. 12]

$$R^7R^8R^9R^{10}N^+Cl^- \quad (4)$$

(In the formula, $R^7$, $R^8$, $R^9$ and $R^{10}$ represent alkyl group having 1 to 4 carbon atoms independently from each other.)

Tetrabutyl ammonium chloride (which may be referred to as "TBAC" hereinafter) is particularly preferable as the above-mentioned tetraalkyl ammonium chloride. Particularly, when the alkali metal fluoride is potassium fluoride dihydrate, the addition of TBAC to potassium fluoride dihydrate is preferable. This kind of the catalyst composition can be prepared by agitating commercially available TBAC with potassium fluoride dihydrate in an acetonitrile solution and drying the resultant solution. It is preferable to blend tetraalkyl ammonium chloride represented by formula (4) in an amount within a range of 0.6 to 40 parts by mass to 100 parts by mass of alkali metal fluoride.

As a fifth catalyst activator, calcium fluoride may be used. In the case of a catalyst composition using potassium fluoride as alkali metal fluoride and using calcium fluoride as a catalyst activator, it is preferable to use the integrated combination of a catalyst and a catalyst activator, in which potassium fluoride and calcium fluoride form potassium calcium trifluoride (chemical formula: $KCaF_3$). Potassium calcium trifluoride can be obtained by vigorously pulverizing potassium fluoride and calcium fluoride mechanically, thereby activating them. Or, potassium calcium trifluoride may be prepared by making potassium fluoride be supported on the surface of calcium fluoride (chemical formula: $CaF_2$) particles and annealing the particles to thereby form $KCaF_3$ on the surface of the particles. It is preferable to blend calcium fluoride in an amount within a range of 30 to 150 parts by mass to 100 parts by mass of alkali metal fluoride.

As a sixth catalyst activator, oligo(ethylene glycol)dimethyl ether (which may be referred to as "glyme" hereinafter) represented by formula (5) may be used.
[Chem. 13]

$$H_3C-O-(CH_2CH_2O)_m-CH_3 \quad (5)$$

(In the formula, m is an integer of from 2 to 8.)

The catalyst composition using the above catalyst activator can be obtained, for example, by impregnating potassium fluoride particles directly with hexaglyme: i.e. a compound of formula (5) in which m is 6 on heating at 60° C. It is preferable to blend oligo(ethylene glycol)dimethyl ether represented by formula (5) in an amount within a range of 40 to 1,000 parts by mass to 100 parts by mass of alkali metal fluoride.

The catalyst composition in the method of the present invention is used in the solid state in most cases.

The catalyst composition containing alkali metal oxide and the above organic catalyst activator can be prepared by several appropriate methods.

A general procedure for preparing a catalyst composition is mixing dispersed alkali metal fluoride and a catalyst activator added thereto and subjecting the mixture to the subsequent treatment as needed. The general method is a method of impregnating the surface of the solid dispersion of alkali metal fluoride with a polar organic solvent solution of the catalyst activator, thereby making the catalyst activator be supported on the surface of the solid dispersion.

Another method for preparing a catalyst composition is treating granulated alkali metal fluoride with a catalyst activator, followed by the heat treatment. As an example of other preparation methods, when commercially available calcium dihydrate tablets are used as a catalyst activator, the tablets can be used as a support supporting alkali metal fluoride.

It is effective to use the thus-obtained catalyst composition in an amount of at least 0.02 parts by mass to 100 parts by mass of alkoxysilane as a starting material. The catalyst composition is used in an amount of from 0.02 to 50 parts by mass generally, and preferably in an amount of from 0.1 to 20 parts by mass.

The dismutation reaction can be performed either in a batch mode or a continuous flow mode. Alkoxysilane represented by formula (1) used as a starting material and the catalyst composition do not have high chemical reactivity. Therefore, the process can be carried out without particular limitations on the material of the apparatus.

Accordingly, various types of reactors can be used in the process and therefore the process can be said to be a catalyst system suitable for an industrial production process.

As to the reaction temperature of the dismutation reaction, it is preferable to perform the reaction upon heating. The preferable temperature varies depending on alkoxysilane to be used as a starting material and is preferably in a range of from 100 to 200° C.

The reaction pressure of the dismutation reaction can be set within a range of from 0.2 to 10 atmospheres. Since the reaction is not highly pressure-dependent, it is preferable to perform the process under atmospheric pressure.

It is known that monosilane as a reaction product is ready to ignite on contact with air. Therefore, to prevent the reaction medium from igniting on exposure to air, it is preferable to perform the reaction under inert gas atmosphere such as nitrogen and argon.

Monosilane produced by the reaction has a boiling point of −111.9° C. and collected in the form of gas after being taken out from the reactor. When the reaction is performed in a batch method, tetraalkoxysilane remains in the reactor. When a reactor of a flow method is used, trialkoxysilane unreacted with tetraalkoxysilane passes through the reactor, tetraalkoxysilane is condensed and trialkoxysilane is to be returned to the catalyst reactor. The catalyst used in the present invention is insoluble both in starting materials and a reaction product, and can be used for a long-term operation period.

EXAMPLES

The invention will be described with reference to Examples below, but the invention is not limited thereto.

Comparative Example 1

Active potassium fluoride was prepared by slowly evaporating a solvent of a solution of potassium fluoride and dried methanol (1:13 to 20 parts by mass) under reduced pressure so as to recrystallize potassium fluoride and then drying it while raising the temperature.

It is preferable not only to use the methanol for purification having purity higher than 99.9% which complies with US Pharmacopeia tests by A. C. S. but also to use dry nitrogen atmosphere. In the process of evaporating methanol, the temperature is preferably 25 to 35° C.

The subsequent process of drying in vacuum should be performed at least for 5 to 6 hours within the temperature range of 75 to 120° C. The alumina having potassium fluoride supported thereon is prepared as follows. 30 g of neutral alumina having a particle diameter of 0.3 to 1.0 mm and 20 g of potassium fluoride are mixed with 200 ml deionized water.

A solvent is evaporated at 50 to 60° C. while being lightly deaerated. The remaining product is dried for three hours while being deaerated.

The process for preparing monosilane and tetraalkoxysilane was performed as follows.

1.0 g of alumina on which potassium fluoride is supported was charged in a reaction tube made of Pyrex (registered trademark) glass provided with an electric furnace and heated to 120° C. The mixture of evaporated trimethoxysilane (flow rate: 3.5 ml/min.) and helium (flow rate: 35 ml/min.) was heated to 120° C. in a preheater and next supplied to a reaction tube to thereby perform dismutation reaction at 120° C. The reaction mixture in the form of gas taken out from the reaction tube was subjected to gas chromatography (GC) analysis for every 20 minutes.

The ratio of unreacted trimethoxysilane, monosilane and tetramethoxysilane ten minutes after the reaction had started was substantially constant in the reaction product. Dimethoxysilane and monomethoxysilane were not detected the first one hour after the reaction had started.

The analysis after performing the reaction in a flow reactor system for five hours showed the following results.

That is, the trimethoxysilane conversion was 63%, the yield of monosilane to the supplied trimethoxysilane was 63% (the yield of monosilane to the converted trimethoxysilane was 100%) and the yield of tetramethoxysilane to the supplied trimethoxysilane was 63% (the yield of tetramethoxysilane to the converted trimethoxysilane was 100%). No by-product was found by the gas chromatography.

Examples 1 to 6

The activity of the catalyst compositions based on potassium fluoride using the various catalyst activators shown in Table 1 was tested and the results are shown in Table 1. The dismutation reaction of trimethoxysilane and the analysis of the product were performed in the same way as in Comparative Examples. The characteristics of the methods for preparing the catalyst compositions are also shown in Table 1. Potassium fluoride was prepared in the same way as in Comparative Examples.

In all the Examples shown in Table 1, no product other than monosilane and tetramethoxysilane was detected by the gas chromatography analysis, and no other reaction product such as alcohol and dimers of hexamethoxydisiloxane was found in the reaction mixture.

Accordingly, the selectivity of the process was 100% with respect to the converted trimethoxysilane.

All the used catalysts were insoluble in the starting materials and reaction products. No mass decrease of the catalysts was observed during the reaction. No decrease in the catalyst activity was observed during the five-hour reaction, either.

The results in Table 1 show that the catalyst efficiency is high in the present invention. These results can be attained by the reaction in a flow reactor system, and the method can be easily applied to the production of monosilane and tetraalkoxysilane on a continuous industrial scale.

Comparative Example 2

Comparative experiments were performed on the catalyst activity of the catalyst activator alone without using alkali metal fluoride. These comparative experiments were performed under the conditions as described in Comparative Example 1. The catalyst activator was applied onto the alumina support in the same way as in Comparative Example 1.

As a result, it was found that the catalyst activator itself has low catalyst activity, and the trimethoxysilane conversion was less than 14%. Only the TBAC supported on alumina was found to have trimethoxysilane conversion of 26% and selectivity of 66%. Accordingly, it was found that the catalyst activator itself had low catalyst activity.

Examples 7 to 12

The catalyst activity of other catalyst compositions was tested and the results are shown in Table 1. The dismutation reaction of trimethoxysilane and the analysis of the products were performed in the same way as in Comparative Examples. The catalyst compositions using the same types of the catalyst activators as those used in Examples 1 to 6 were prepared in the same way as the corresponding catalyst compositions of Examples 1 to 6. Alkali metal fluorides such as potassium fluoride were prepared in a similar way to Comparative Example 1.

Regarding the selectivity, the mole percent ratio of tetraalkoxysilane to the total amount of monoalkoxysilane, dialkoxysilane, trialkoxysilane and tetraalkoxysilane was calculated. Other impurities such as alcohol and siloxane dimer were not detected in the reaction products.

The results in Table 1 show that the tested catalyst compositions have high catalyst efficiency.

When the time of contact between the gaseous reaction mixture and the catalyst in the reactor is longer, the conversion tends to improve. For example, when the flow rate of helium gas was changed from 35 ml/min. to 70 ml/min. and 150 ml/min., the trimethoxysilane conversion changed from 89% to 52% and 33%, respectively. That is, the shorter time of contact between the catalyst and the reaction mixture lowers the conversion.

TABLE 1

| Examples | Alkali metal fluoride | Amount (Parts by mass) | Catalyst activator | Amount (Parts by mass) | Alkoxysilane conversion/ selectivity (%) |
| --- | --- | --- | --- | --- | --- |
| 1 | Potassium fluoride | 100 | TDAPB | 3 | 83/100 |
| 2 | Potassium hydrogen fluoride | 100 | DABCO | 5 | 95/100 |
| 3 | Potassium fluoride | 100 | HEGC | 4 | 89/100 |
| 4 | Potassium fluoride dihydrate | 100 | TBAC | 25 | 85/100 |
| 5 | Potassium fluoride | 100 | Calcium fluoride | 130 | 81/100 |
| 6 | Potassium fluoride | 100 | Hexaglyme | 500 | 76/100 |
| 7 | Sodium fluoride | 100 | TDAPB | 10 | 51/92 |
| 8 | Cesium fluoride | 100 | DABCO | 3 | 97/100 |
| 9 | Potassium fluoride | 100 | DABCO | 10 | 94/100 |
| 10 | Cesium fluoride | 100 | HEGC | 20 | 95/85 |
| 11 | Cesium fluoride | 100 | Calcium fluoride | 100 | 72/68 |
| 12 | Potassium fluoride | 100 | Tetraglyme | 700 | 54/57 | catalyst composition of Example 1: prepared by dipping potassium fluoride particles in a TDABP solution and drying the solution catalyst composition of Example 2: prepared by dipping potassium hydrogen fluoride pellets in a DABCO solution, drying the solution and subjecting the solution to heat treatment catalyst composition of Example 3: prepared by dipping potassium fluoride particles in a HEGC solution and drying the solution catalyst composition of Example 4: prepared by adding TBAC to an acetonitrile solution having potassium fluoride dihydrate dispersed therein, stirring and drying the solution catalyst composition of Example 5: prepared by kneading potassium fluoride and calcium fluoride powders, heating the mixture and molding the heated mixture in the form of pellets catalyst composition of Example 6: prepared by directly impregnating potassium fluoride particles with a hexaglyme compound at 60° C.

alkoxysilane of Examples 1 to 6: trimethoxysilane
alkoxysilane of Example 7: triethoxysilane
alkoxysilane of Example 8: trimethoxysilane
alkoxysilane of Example 9: diethoxysilane
alkoxysilane of Example 10: methoxysilane
alkoxysilane of Example 11: dimethoxysilane
alkoxysilane of Example 12: ethoxysilane

The invention claimed is:

1. A method for producing monosilane and tetraalkoxysilane comprising subjecting alkoxysilane represented by formula (1)

$$H_nSi(OR)_{4-n} \qquad (1)$$

wherein R represents alkyl group having 1 to 6 carbon atoms and n represents an integer of from 1 to 3, to dismutation reaction in a gaseous phase in the presence of a catalyst containing an alkali metal fluoride and a catalyst activator from the group consisting of the following (i) to (vi):

(i) tetrakis(dialkylamino)phosphonium halide represented by formula (2)

$$(R^1R^2N)_4P^+X^- \qquad (2)$$

wherein $R^1$ and $R^2$ represent alkyl group having 1 to 3 carbon atoms independently from each other and X represents Br, Cl or F;

(ii) 1,4-diazabicyclo[2.2.2] octane;

(iii) hexaalkyl guanidinium halide represented by formula (3)

$$[(R^3R^4N)_2CNR^5R^6]^+X^- \qquad (3)$$

wherein $R^3$, $R^4$, $R^5$ and $R^6$ represent alkyl group having 1 to 3 carbon atoms independently from each other and X represents Br, Cl or F;

(iv) tetraalkyl ammonium chloride represented by formula (4)

$$R^7R^8R^9R^{10}N^+Cl^- \qquad (4)$$

wherein $R^7$, $R^8$, $R^9$ and $R^{10}$ represent alkyl group having 1 to 4 carbon atoms independently from each other;

(v) calcium fluoride; and (vi) oligo(ethylene glycol) dimethyl ether represented by formula (5)

$$H_3C-O-(CH_2CH_2O)_m-CH_3 \qquad (5)$$

wherein m is an integer of 2 to 8.

2. The method as claimed in claim 1, wherein the alkali metal fluoride is potassium fluoride.

3. The method as claimed in claim 2, wherein potassium fluoride is potassium fluoride dihydrate.

4. The method as claimed in claim 1, wherein tetrakis(dialkylamino)phosphonium halide is tetrakis(diethylamino)phosphonium bromide.

5. The method as claimed in claim 1, wherein hexaalkyl guanidinium halide is hexaethyl guanidinium chloride.

6. The method as claimed in claim 1, wherein tetraalkyl ammonium chloride is tetrabutyl ammonium chloride.

7. The method as claimed in claim 2, wherein the alkali metal fluoride is potassium fluoride, the catalyst activator is calcium fluoride, potassium fluoride and calcium fluoride form potassium calcium trifluoride, and the integrated combination of the catalyst and the catalyst activator is used.

8. The method as claimed in claim 1, wherein n in formula (1) is 1.

9. The method as claimed in claim 8, wherein alkoxysilane represented by formula (1), in which n is 1, is trimethoxysilane.

* * * * *